(12) United States Patent
Greb et al.

(10) Patent No.: US 8,445,728 B2
(45) Date of Patent: May 21, 2013

(54) METHOD FOR REPROCESSING A LIQUID HYDROFORMYLATION PRODUCT

(75) Inventors: Wolfgang Greb, Dinslaken (DE); Rainer Lukas, Essen (DE); Klaus Schmid, Dinslaken (DE); Wolfgang Zgorzelski, Oberhausen (DE); Jörg Arnold, Dinslaken (DE)

(73) Assignee: Oxea GmbH, Oberhausen (DE)

( * ) Notice: Subject to any disclaimer, the term of this patent is extended or adjusted under 35 U.S.C. 154(b) by 83 days.

(21) Appl. No.: 13/138,813

(22) PCT Filed: Mar. 18, 2010

(86) PCT No.: PCT/EP2010/001719
§ 371 (c)(1),
(2), (4) Date: Oct. 3, 2011

(87) PCT Pub. No.: WO2010/115511
PCT Pub. Date: Oct. 14, 2010

(65) Prior Publication Data
US 2012/0108852 A1 May 3, 2012

(30) Foreign Application Priority Data
Apr. 7, 2009 (DE) .......................... 10 2009 016 652

(51) Int. Cl.
*C07C 45/50* (2006.01)

(52) U.S. Cl.
USPC ............................................ 568/451; 568/454

(58) Field of Classification Search
USPC .................................................. 568/451, 454
See application file for complete search history.

(56) References Cited

U.S. PATENT DOCUMENTS

| | | | |
|---|---|---|---|
| 4,148,830 A | 4/1979 | Purett et al. | 260/604 HF |
| 4,247,486 A | 1/1981 | Brewester et al. | 568/454 |
| 4,283,562 A | 8/1981 | Billing et al. | 568/454 |

FOREIGN PATENT DOCUMENTS

| | | |
|---|---|---|
| EP | 0 805 138 | 4/1997 |
| WO | 96/34687 | 11/1996 |
| WO | 97/07086 | 2/1997 |
| WO | 01/58844 | 8/2001 |

OTHER PUBLICATIONS

International Search Report, May 4, 2010.
International Preliminary Report on Patentability, completed Oct. 18, 2011.

*Primary Examiner* — Sikarl Witherspoon
(74) *Attorney, Agent, or Firm* — Michael W. Ferrell

(57) ABSTRACT

The invention relates to a method for reprocessing a liquid product of a hydroformylation reaction, wherein the liquid phase produced in a release stage is supplied to a separating device from which a liquid flow containing rhodium is guided away via a filter, where solids thereby separated are taken out of the process and the filtrate obtained is guided back into the hydroformylation reaction.

20 Claims, 1 Drawing Sheet

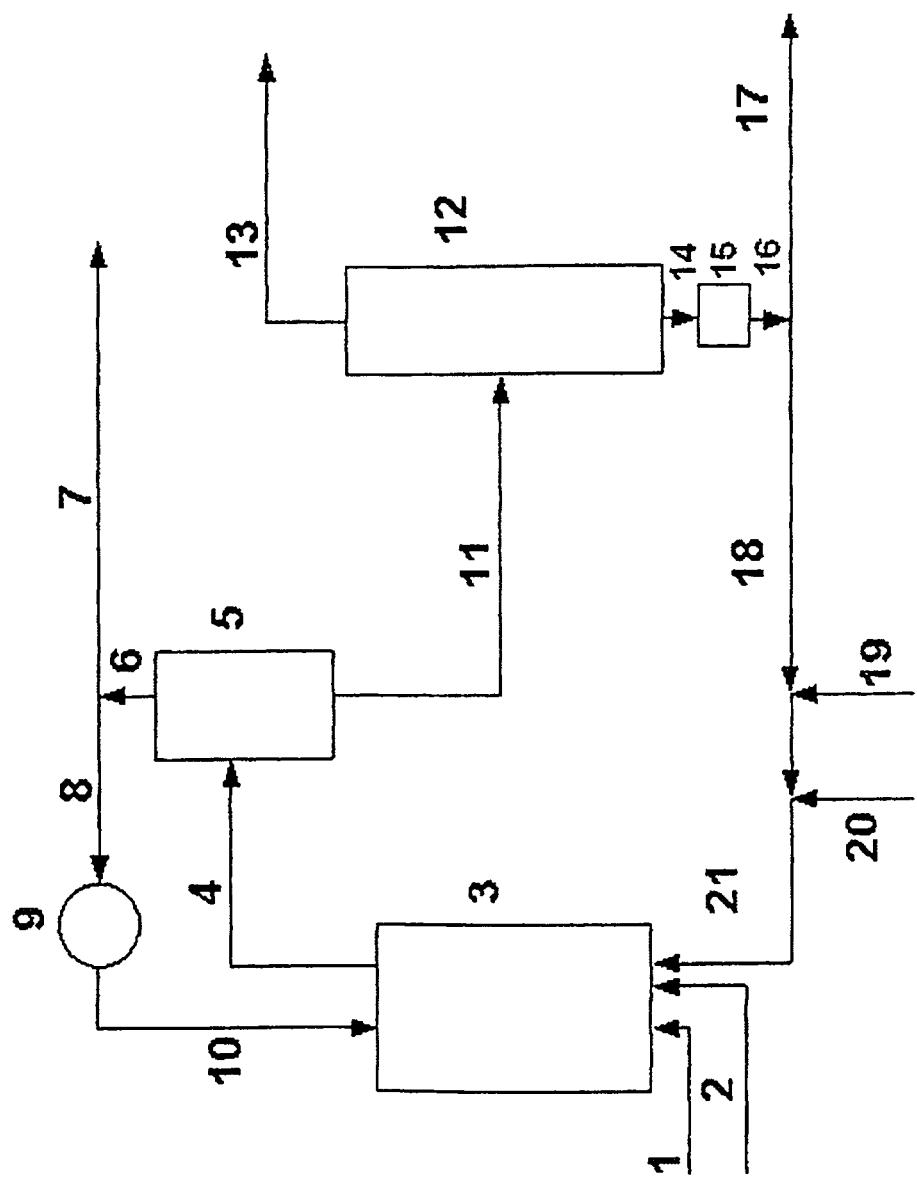

METHOD FOR REPROCESSING A LIQUID HYDROFORMYLATION PRODUCT

CLAIM OF PRIORITY

This application is based on International Patent Application No. PCT/EP2010/001719 (International Publication No. WO 2010/115511), filed Mar. 18, 2010, entitled "Verfahren Zur Aufarbeitung Eines Flüssigen Hydroformylierungsaustrags", which was based on German Application No. DE 10 2009 016 652.1, filed Apr. 7, 2009. The priorities of the foregoing applications are hereby claimed and their disclosures incorporated herein by reference in their entireties.

TECHNICAL FIELD

The invention relates to a process for working up a liquid hydroformylation output from a hydroformylation reaction, which output contains at least one aldehyde as hydroformylation product, unreacted olefinically unsaturated compounds, dissolved synthesis gas, the homogeneously dissolved hydroformylation catalyst and by-products of the hydroformylation reaction.

BACKGROUND

It is known that compounds containing olefinic double bonds can be reacted with carbon monoxide and hydrogen to form aldehydes (oxo process). The process is not restricted to the use of olefinic hydrocarbons but also extends to starting materials which have not only the double bond but also functional groups, predominantly groups which remains unaltered under the reaction conditions.

The classical oxo process is carried out using cobalt as catalyst. Its effectiveness is based on the formation of cobalt carbonyl compounds by action of hydrogen and carbon monoxide on metallic cobalt or cobalt compounds at pressures above 20 MPa and temperatures of about 120° C. and above.

During the further development of the oxo process, cobalt has been increasingly replaced by rhodium as catalyst metal. Rhodium is used as a complex preferably containing phosphines as ligands in addition to carbon monoxide. Rhodium as metal allows the process to be carried out at lower pressures, and in addition higher yields are achieved and the unbranched products which are more valuable for further processing are preferentially formed when straight-chain terminal olefins are used as starting materials.

Industrially, the hydroformylation of olefinically unsaturated compounds is carried out under the catalytic action of rhodium carbonyl complexes having tertiary organic phosphines or phosphites as ligands. In one process variant, the reaction is carried out in a homogeneous organic phase, i.e. olefinically unsaturated compound used, catalyst and the reaction products of the hydroformylation reaction are present together in solution. The reaction products are usually separated off from the mixture by distillation, more rarely by other methods such as extraction. The hydroformylation process carried out in the homogeneous phase can be configured as a gas recycle process as described in U.S. Pat. No. 4,247,486 A1 or in the form of a liquid recycle process as described in U.S. Pat. No. 4,148,830 A1.

High-boiling aldehyde condensation products, which comprise a complex mixture of oxygen-containing compounds which are formed from the initially formed aldehydes by means of condensation reactions such as the aldol reaction or by the Tishchenko reaction and have different degrees of condensation, are formed as by-products in the hydroformylation reaction.

The formation of, for example, dimers, trimers or tetramers as high-boiling aldehyde condensation products in the hydroformylation reaction carried out homogeneously is described, for example, in U.S. Pat. No. 4,148,830 A1. These high-boiling aldehyde condensation products are suitable as solvent for the homogeneously dissolved rhodium catalyst. In addition, they stabilize the rhodium catalyst both in the hydroformylation reaction and in the subsequent work-up steps for the liquid hydroformylation output. However, to prevent their concentration in the liquid phase from increasing too greatly, part always has to be removed from the hydroformylation process. In steady-state operation of the hydroformylation plant, the high-boiling aldehyde condensation products are discharged in the same amount in which they are formed.

In the liquid recycle process as described in U.S. Pat. No. 4,148,830 A1, the liquid output from the hydroformylation reaction is firstly depressurized into a depressurization vessel in which separation into a gas phase and a liquid phase occurs. The liquid phase contains essentially the catalyst, high-boiling aldehyde condensation products, solvent, the desired aldehyde and small amounts of unreacted olefinically unsaturated compound. The gas phase contains excess synthesis gas, inerts and hydrogenated products, small amounts of the aldehyde formed and also unreacted olefinically unsaturated compounds. After a proportion of inerts and hydrogenation products have been separated off and removed, the gas phase is compressed and recirculated to the hydroformylation reactor. The liquid catalyst-containing stream is fed to a separation apparatus, preferably a distillation apparatus, from which the desired aldehydes and small amounts of dissolved synthesis gas and olefinically unsaturated compound are taken off as overhead product. The mixture is then separated into the pure n- and iso-aldehydes in a further purification step. The rhodium-containing stream obtained, which additionally contains the high-boiling aldehyde condensation products as solvent, is recirculated to the hydroformylation reactor.

WO 01/58844 A2 relates to the work-up of a liquid output from a hydroformylation reaction which is carried out continuously. In the known process, a two-stage depressurization is carried out, with depressurization to a pressure which is from 0.2 to 2 MPa below the reaction pressure being carried out in the first stage. The resulting liquid phase is depressurized further in a second, lower-pressure stage to form a gas phase which contains essentially the major part of the desired hydroformylation product. The liquid phase obtained, which contains high-boiling by-products and the homogeneously dissolved hydroformylation catalyst, is recirculated either directly or after work-up by distillation to the hydroformylation reactor.

It is known that decomposition and/or deactivation of the rhodium catalyst can occur in the work-up by distillation of the reactor output from the rhodium-catalyzed hydroformylation reaction carried out homogeneously. Such decomposition and/or deactivation can result, firstly, in precipitation of insoluble rhodium compounds or rhodium metal which deposit as deposits or coatings in the apparatuses and can no longer be recirculated in the hydroformylation process carried out homogeneously. Such amounts of rhodium are, firstly, no longer available to the ongoing process and can only be recovered from the apparatuses by means of specific cleaning measures during a shutdown of the plant. Furthermore, rhodium-containing solids formed by decomposition and deactivation can be present in suspended and thus pumpable form in the distillation residue and be able to be recirculated to the hydroformylation reactor, but such suspended rhodium-containing solids frequently have only a low hydroformylation activity. This can likewise apply to decomposition and deactivation products which are present in dissolved form in the distillation residue. To maintain a prescribed space-time yield of aldehyde, it is therefore necessary to introduce more rhodium in the form of fresh rhodium catalyst than the amount of rhodium taken off with the high-boiling aldehyde condensation products formed. The difference between the amount of fresh rhodium added and the amount of deactivated rhodium discharged remains in the plant and initially counts as rhodium consumption.

It is therefore an object of the invention to provide a process for working up a liquid output from a hydroformylation reaction, in which the decomposition and/or deactivation of the homogeneously dissolved rhodium complex catalyst can be suppressed effectively.

SUMMARY OF INVENTION

The invention accordingly provides a process for working up a liquid output from a hydroformylation reaction, which output contains aldehyde, high-boiling by-products of the hydroformylation reaction, a homogeneously dissolved rhodium complex catalyst, unreacted olefinically unsaturated compound, synthesis gas and volatile by-products, in which
 a) the liquid hydroformylation output is depressurized in a depressurization vessel, resulting in separation into a liquid phase and a gas phase; and
 b) the liquid phase obtained in the depressurization vessel is introduced into a separation apparatus in which separation into a liquid phase containing essentially high-boiling by-products of the hydroformylation reaction, the homogeneously dissolved rhodium complex catalyst and small amounts of the aldehyde and a gas phase containing the predominant amount of the aldehyde is carried out; and
 c) a liquid, rhodium-containing output is discharged from the separation apparatus,
 characterized in that the liquid, rhodium-containing output discharged from the separation apparatus is passed through a filter and solids separated off are removed from the process while the filtrate obtained is recirculated to the hydroformylation reaction.

BRIEF DESCRIPTION OF DRAWING

The invention is described in detail below in connection with the accompanying FIG. 1 which is a schematic diagram illustrating a process of the invention.

DETAILED DESCRIPTION

The process of the invention is suitable for working up a liquid, rhodium-containing output from a hydroformylation reaction carried out in a homogeneous reaction system. For the purposes of the present invention, the term homogeneous reaction system refers to a homogeneous solution composed essentially of solvent, catalyst, olefinically unsaturated compound and reaction product. Rhodium complexes containing organic phosphorus(III) compounds as ligands are used as catalyst. Such complexes and their preparation are known (for example U.S. Pat. No. 3,527,809 A1, U.S. Pat. No. 4,148,830 A1, U.S. Pat. No. 4,247,486 A1, U.S. Pat. No. 4,283,562 A1). They can be used as uniform complex or as a mixture of various complexes. The rhodium concentration in the reaction medium extends over a range from about 1 to about 1000 ppm by weight and is preferably from 10 to 500 ppm by weight. In particular, rhodium is used in concentrations of from 10 to 200 ppm by weight, in each case based on the olefinically unsaturated compound used. The rhodium complex having the stoichiometric composition can be employed as catalyst. However, it has been found to be advantageous to carry out the hydroformylation in the presence of a catalyst system composed of the rhodium complex and free, i.e. excess, phosphorus ligand which no longer forms a complex with rhodium. The free phosphorus ligand can be the same as that in the rhodium complex, but ligands different from this can also be used. The free ligand can be a uniform compound or consist of a mixture of various organophosphorus compounds. Examples of rhodium complexes which are employed as catalysts are described in U.S. Pat. No. 3,527,809 A1. Preferred ligands in the rhodium complex catalysts include, for example, triarylphosphines such as triphenylphosphine, trialkylphosphines such as tri(n-octyl)phosphine, tri(cyclohexyl)phosphine, alkylphenylphosphines, cycloalkylphenylphosphines and organic phosphites, for example tris(2,4-di-t-butylphenyl) phosphite or the bisphosphites known from WO 96/34687 A1. Owing to its ready availability, triphenylphosphine or tri(2,4-di-t-butylphenyl) phosphite are particularly frequently employed.

The molar ratio of rhodium to phosphorus is usually from 1:1 to 1:300, but the mol fraction of phosphorus in the form of organic phosphorus compounds can also be higher. Rhodium and organically bound phosphorus are preferably used in molar ratios of from 1:3 to 1:200.

When triarylphosphines are employed, Rh/P molar ratios of from 1:30 to 1:150 have been found to be particularly useful.

The hydroformylation reaction is carried out in the presence of a solvent. Organic compounds in which the starting material, reaction product and catalyst system are soluble are used as solvents. Examples of such compounds are aromatic hydrocarbons such as benzene, toluene or the xylenes. Other solvents which can be used are paraffin oil, ketones or ethers. The high-boiling condensation compounds of the aldehydes, which are formed as high-boiling by-products in the hydroformylation reaction, have been found to be particularly useful solvents. The proportion of solvent in the reaction medium can be varied over a wide concentration range and is usually in the range from 10 to 90% by weight, preferably from 10 to 50% by weight, based on the reaction mixture.

The hydroformylation reaction is generally carried out at a pressure of from 0.5 to 40 MPa, preferably from 0.5 to 10 MPa, but higher pressures of from 10 to 40 MPa can also be employed. The use of such high pressures in the hydroformylation reaction carried out homogeneously using rhodium complexes is known from EP 0 805 138 A1.

The reaction temperature is generally from 50 to 160° C. Temperatures of from 60 to 150° C. and in particular from 75 to 140° C. are preferred.

The molar ratio of hydrogen to carbon monoxide in the synthesis gas is from 1:10 to 10:1, preferably from 1:3 to 3:1 and in particular 1:1. At the temperatures indicated and the pressure indicated, the synthesis gas used in excess for the hydroformylation is dissolved in an amount corresponding to its solubility in the liquid hydroformylation output.

The liquid hydroformylation output is firstly depressurized in a depressurization stage, resulting in separation into a liquid phase and a gas phase. The gas phase obtained contains essentially excess synthesis gas, unreacted olefinically unsaturated compound, hydrogenated products and inert gases from the process for producing synthesis gas. The gas phase is, after part of the inerts have been separated off, compressed again and recirculated to the hydroformylation reaction. The liquid phase obtained contains essentially the aldehyde, high-boiling by-products of the hydroformylation reaction, e.g. high-boiling aldehyde condensation products, rhodium complexes and dissolved synthesis gas. If a further organic solvent such as toluene or xylene is added, this is also present. However, preference is given to using the high-boiling aldehyde condensation products as solvents without addition of a further organic solvent. The depressurization serves to remove gaseous components dissolved in the liquid output and is therefore carried out at a pressure which is lower than the pressure in the hydroformylation reactor. The pressure in the depressurization vessel can be set over a wide range. It can be only slightly lower than the reactor pressure and in general correspond to the pressure drop between the reactor and the downstream depressurization vessel. However, depressurization can also be carried out to a lower pressure, for example to a pressure in the range from 0.1 to 1.5 MPa, preferably from 0.3 to 1.0 MPa.

The liquid phase separated out in the depressurization vessel is subsequently discharged and introduced into a separation apparatus in which the desired aldehyde is separated from the homogeneously dissolved hydroformylation catalyst. Here, the liquid phase is depressurized to a pressure which is lower than the pressure in the depressurization vessel. A gaseous phase which contains the major part of the desired aldehydes together with residual amounts of synthesis gas and low-boiling compounds, for example alkanes formed by hydrogenation, is formed. The n- and iso-aldehydes are subsequently isolated from the discharged gas phase in further purification steps. The liquid phase discharged from the separation apparatus contains the homogeneously dissolved hydroformylation catalyst, high-boiling aldehyde condensation products and organic solvent, if added.

In general, depressurization is carried out to atmospheric pressure. The separation apparatus is operated at a temperature of up to 160° C., preferably from 100 to 140° C. To keep damage to the hydroformylation catalyst as low as possible during its separation from the desired aldehydes, the temperature must not exceed 160° C. The separation apparatus can have any configuration which allows the hydroformylation catalyst to be separated thermally from the aldehyde. It is possible to use, for example, a flash distillation apparatus without internals or a conventional distillation column which may be provided with random packing elements such as Raschig rings, spirals or saddles, ordered packing or internals such as trickle trays to improve the separation performance. The distillation conditions such as temperature and pressure depend on the physical properties of the desired aldehydes.

It is likewise possible to arrange further depressurization vessels in which depressurization is carried out to a decreasing pressure from stage to stage between the depressurization vessel arranged downstream of the hydroformylation reactor and the separation apparatus serving to separate aldehyde from the rhodium complex catalyst. This cascade-like arrangement is advantageous particularly when the hydroformylation reaction is carried out at relatively high pressures. The gaseous phases obtained, which contain residual synthesis gas, unreacted olefinically unsaturated compound, inerts and further volatile components, are discharged and removed from the process or advantageously partly removed and after compression of the remainder recirculated to the hydroformylation reactor. The liquid phase obtained in the respective depressurization stage, in which the desired aldehyde and the hydroformylation catalyst are present as a solution in the high-boiling aldehyde condensation products, is introduced into the next depressurization stage. The liquid phase taken off from the last depressurization vessel is then introduced into the separation apparatus for separating the aldehyde from the hydroformylation catalyst. To stabilize the rhodium catalyst, it is advantageous to set a carbon monoxide partial pressure of from 0.05 to 0.35 MPa, preferably from 0.1 to 0.3 MPa, in the gas phase in the depressurization vessel or vessels. Depending on the solubility prevailing at the temperatures and pressures set, carbon monoxide is present as a solution in the liquid, organic phase and is able to stabilize the rhodium complex catalyst.

The liquid stream taken off at the bottom of the separation apparatus, which consists essentially of high-boiling aldehyde condensation products and organic solvent, if added, and in which the rhodium complex catalyst is present as a homogeneous solution and which contains further rhodium compounds of lower catalytic activity partly in suspended form, is passed through a filter in order to separate off suspended solids. These partly rhodium-containing solids have been found to be harmful and can, after recirculation to the hydroformylation zone and into the downstream depressurization vessels and separation apparatuses, damage the rhodium complex catalyst and promote precipitation of further rhodium-containing solids and thus contribute to rhodium losses.

Suitable filter media are materials customary in the industry, e.g. glass fibers or metal fibers or polymer fibers, for example fibers composed of polypropylene, as long as they have sufficient chemical resistance to the organic liquid. In addition, the filter devices installed have to have sufficient mechanical stability to stress. Commercially available candle filters or fiberglass filter cartridges having a metal core have been found to be particularly useful. To avoid building up an excessively high filtration resistance, the pore size of the filter material should be greater than 0.1 μm. On the other hand, materials which have too wide a mesh opening are likewise unsuitable because of an excessively low separation effect. Filters having a pore size in the range from 0.1 to 20 μm, preferably from 0.5 to 10 μm, are particularly advantageous.

As soon as the filter has accumulated too much deposit, it is removed from the apparatus. The solids deposited thereon, which partially contain rhodium, are worked up separately in order to recover the noble metal and thus minimize the rhodium consumption.

Without wishing to go into great detail with regard to mechanistic considerations, it can be assumed that the solids present in the recirculated liquid stream, which comprise abrasion from the plants or rhodium-containing deactivation and decomposition products of the hydroformylation catalyst, known as rhodium clusters, act as crystallization nuclei and accelerate the conversion of the catalytically active rhodium compounds into inactive solids. Such solids not only damage the catalytically active rhodium compounds present in the liquid phase but also promote cluster formation from freshly introduced rhodium compounds. Fresh rhodium has to be added firstly to replace the amounts of rhodium discharged via the high-boiling aldehyde condensation products and secondly to compensate the decrease in activity of the rhodium complexes remaining in the hydroformylation process. The measure according to the invention of removing harmful solids from the liquid stream recirculated to the hydroformylation reaction by means of a filter makes it possible to add less fresh rhodium per kilogram of olefinically unsaturated compound used to achieve a desired space-time yield of aldehyde compared to a mode of operation in which the liquid stream discharged from the separation apparatus is recirculated to the hydroformylation reaction without use of a filter. In the process of the invention, generally from 0.5 to 3 ppm by weight of fresh rhodium, based on olefinically unsaturated compound used, are necessary. This contrasts with an increased addition of fresh rhodium of in addition from 0.5 to 1 ppm by weight, based on olefinically unsaturated compound used, if no filter is employed. Correspondingly higher rhodium consumptions then result.

The liquid product stream obtained after passage through the filter is partly discharged in order to avoid accumulation of the aldehyde condensation products. In steady-stage operation of the hydroformylation plant, the concentration of aldehyde condensation products remains constant since the amount formed during the hydroformylation reaction corresponds approximately to the amount discharged. The undischarged rhodium-containing liquid stream which has been freed of solids is recirculated to the hydroformylation reaction.

In a further embodiment of the process of the invention, a substream is firstly taken off from the rhodium-containing, liquid output from the bottom of the separation apparatus and discharged in order to avoid accumulation of the high-boiling aldehyde condensation products. The other substream to be recirculated is passed through the filter to separate off solids.

Fresh rhodium and free organic phosphorus(III) compound, preferably the phosphorus compound used in the catalytic process, are added to the rhodium-containing liquid stream which has been freed of solids and is recirculated to the hydroformylation reaction before entry into the hydroformylation reaction. The organic phosphorus(III) compound is added in such an amount that the molar ratio of rhodium to phosphorus is from 1:3 to 1:200, preferably from 1:30 to 1:150.

Fresh rhodium is added in the form of rhodium compounds such as rhodium salts, for example salts of aliphatic monocarboxylic and polycarboxylic acids, e.g. rhodium 2-ethylhexanoate, acetate, oxalate, propionate or malonate, salts of inorganic hydrogen acids and oxo acids, e.g. nitrate, sulfate or chloride, rhodium complexes such as cyclopentadienylrhodium compounds, rhodium acetylacetonate, $[RhCl(1,5-cyclooctadiene)]_2$, rhodium carbonyl compounds such as $Rh_3(CO)_{12}$, $Rh_6(CO)_{16}$ or in the form of various rhodium oxides.

The rhodium compound used for the fresh rhodium addition is dissolved in an organic solvent or, depending on the dissolution behavior, suspended in the organic solvent. Advantageous solvents have been found to be the high-boiling aldehyde condensation products or preferably the desired aldehydes.

After addition of free organic phosphorus(III) compound and fresh rhodium, advantageously in the form of rhodium 2-ethylhexanoate, to the recirculated, rhodium-containing solution, the solution which has been adjusted in this way is returned to the hydroformylation reaction.

The reaction can be carried out either batchwise or continuously, with a continuous process being preferred.

The preferred process according to the invention is illustrated below with the aid of the in-principle scheme as per FIG. 1. However, the process of the invention is not restricted to the embodiment depicted in the drawing.

The olefinically unsaturated compound is introduced into the hydroformylation reactor 3 via line 1 and synthesis gas is introduced via line 2. The hydroformylation output is taken off via line 4 and introduced into the depressurization vessel 5. Here, the reaction mixture is brought to a pressure which is lower than the pressure prevailing in the hydroformylation reactor 3. This results in separation into a gas phase which contains predominantly synthesis gas, unreacted olefinically unsaturated compound and volatile compounds and a liquid phase.

The gas phase is discharged via line 6 from the depressurization vessel 5. Part is discharged from the process via line 7 in order to avoid accumulation of inerts. The gas stream discharged can be utilized thermally. The undischarged gas stream is fed via line 8 to a compressor 9 and there brought to the reactor pressure and recirculated via line (10) to the hydroformylation reactor 3.

The liquid phase obtained is fed via line 11 to a separation apparatus 12. The liquid phase contains essentially the aldehydes, high-boiling aldehyde condensation products as high-boiling by-products of the hydroformylation reaction, the rhodium-containing hydroformylation catalyst, further catalytically less active or inactive rhodium complexes and, if used, solvent. In the separation apparatus 12, the desired aldehydes are separated off from the rhodium and high boilers. The separation apparatus 12 is preferably a conventional distillation column which is equipped, for example, with random packing elements, ordered packing or internals for intensive gas/liquid exchange. The aldehydes taken off at the top of the separation apparatus 12 via line 13 are subsequently separated into n- and iso-aldehyde in a further distillation stage (not shown in FIG. 1). The rhodium-containing bottoms from the separation apparatus 12 are discharged at a temperature at the bottom of not more than 150° C. via line 14 and passed through the filter 15, for example a commercially available candle filter composed of glass fibers and having a pore size of from 0.1 to 20 μm. Here, solids, for example abrasion from the plant components or compounds which are formed during the hydroformylation reaction, the depressurization steps and the aldehyde/catalyst separation and are insoluble in the organic liquid are retained. It has been found that such solids present in the organic solution have an adverse effect and promote deactivation and decomposition of the rhodium complex catalyst.

The filtrate which has been freed of solids flows out via line 16 and is partly removed from the process via line 17 in order to avoid accumulation of the high-boiling aldehyde condensation products. Amounts of rhodium present therein are worked up externally. The undischarged stream is conveyed away via line 18 and admixed with fresh rhodium solution brought via line 19 and phosphorus compound brought via line 20. The solution which has been adjusted in this way is then returned via line 21 to the hydroformylation reactor 3. It is likewise possible to mix the fresh rhodium solution with the phosphorus compound beforehand and to add these together to the rhodium-containing filtrate. As soon as the filter 15 has accumulated too large an amount of deposits, it is replaced by a fresh filter. Deposited solids, which partly contain rhodium are worked up separately.

The process of the invention can be applied to olefinically unsaturated compounds of any structure. Accordingly, both olefins having an internal double bond and olefins having a terminal double bond and likewise straight-chain or branched olefins are suitable as starting material. In addition, the olefins can also be substituted by functional groups, in particular functional groups which are not altered during the course of the reaction. Multiply olefinically unsaturated compounds are also possible as starting materials. The process has been found to be particularly useful in the hydroformylation of olefinically unsaturated hydrocarbons having from 2 to 25 carbon atoms in the molecule, preferably ethylene, propylene, 1-butene, mixtures containing 1-butene and 2-butene, 1-hexene, 1-octene, dimeric butenes, trimeric propylene or industrially available olefin mixtures such as Dimersol® or Octol®.

The invention is illustrated in the following example but is not restricted to the embodiments described.

EXAMPLE

Propylene was reacted with a mixture consisting of equal volumes of $CO/H_2$ at a pressure of 5 MPa and a reaction temperature of 132° C. The catalyst consisted of high-boiling aldehyde condensation products in which triphenylphosphine (TPP) and the rhodium complex $HRhCO(TPP)_3$ have been dissolved. The molar ratio of rhodium to phosphorus was 1:80 and the rhodium concentration was 100 ppm, based on propylene used.

The product stream leaving the reactor was firstly depressurized to a pressure of 1.0 MPa into a depressurization vessel. The gas phase obtained in the depressurization vessel was discharged. Part of the discharged gas stream was removed from the process, and the other part was compressed and then recirculated to the reactor.

The liquid phase obtained in the depressurization was fed to a commercial distillation column. At a temperature at the bottom of from 110 to 130° C. and atmospheric pressure, the n/i-butyraldehyde mixture was taken off as overhead product and separated in a further distillation column into n-butyraldehyde and isobutyraldehyde. The rhodium-containing distillation bottoms discharged were subsequently passed through a commercial fiberglass filter cartridge from Fuhr having a metal core and a pore size of 0.5 µm.

The filtrate which had been freed of solids was subsequently divided into two substreams in a mass ratio of 90:10. The substream having the lower mass was taken from the process, while the other substream was, as circulated catalyst, admixed with a solution of fresh rhodium 2-ethylhexanoate in n-butyraldehyde. Fresh triphenylphosphine was added separately therefrom to give a molar ratio of rhodium to phosphorus of 1:80. The rhodium-containing solution which had been adjusted in this way was subsequently recirculated to the hydroformylation reactor.

The filtration of the recirculated, rhodium-containing bottoms from the distillation column surprisingly allows the specific rhodium consumption in the hydroformylation of propylene to be reduced significantly. To obtain a desired space-time yield, only from 0.5 to 3 ppm by weight of fresh rhodium, based on propylene, has to be added in the process of the invention.

In comparison, if the filtration step is not employed, an increased addition of fresh rhodium of in addition from 0.5 to 1 ppm by weight, based on propylene, is necessary.

While the invention has been described in detail, modifications within the spirit and scope of the invention will be readily apparent to those of skill in the art. In view of the foregoing discussion, relevant knowledge in the art and references including co-pending applications discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

The invention claimed is:

1. A process for working up a liquid output from a hydroformylation reaction, which output contains aldehyde, high-boiling by-products of the hydroformylation reaction, a homogeneously dissolved rhodium complex catalyst, unreacted olefinically unsaturated compound, synthesis gas and volatile by-products, in which
    a) the liquid hydroformylation output is depressurized in a depressurization vessel, resulting in separation into a liquid phase and a gas phase; and
    b) the liquid phase obtained in the depressurization vessel is introduced into a separation apparatus in which separation into a liquid phase containing essentially high-boiling by-products of the hydroformylation reaction, the homogeneously dissolved rhodium complex catalyst and small amounts of the aldehyde and a gas phase containing the predominant amount of the aldehyde is carried out; and
    c) a liquid, rhodium-containing output is discharged from the separation apparatus, characterized in that the liquid, rhodium-containing output discharged from the separation apparatus is passed through a filter and solids separated off are removed from the process while the filtrate obtained is recirculated to the hydroformylation reaction.

2. The process as claimed in claim 1, characterized in that part of the liquid, rhodium-containing output discharged from the separation apparatus is removed from the process.

3. The process as claimed in claim 1, characterized in that the separation apparatus is operated at a temperature of up to 160° C.

4. The process as claimed in claim 1, characterized in that a carbon monoxide partial pressure of from 0.05 to 0.35 MPa is set in the gas phase in the depressurization vessel.

5. The process as claimed in claim 1, characterized in that a plurality of depressurization vessels having pressures which decrease from stage to stage are employed.

6. The process as claimed in claim 1, characterized in that glass fibers, metal fibers or polymer fibers are used for the filter.

7. The process as claimed in claim 6, characterized in that the filter has a pore size of from 0.1 to 20 µm.

8. The process as claimed in claim 1, characterized in that fresh rhodium and free organic phosphorus(III) compound are added to the filtrate before entry into the hydroformylation reaction.

9. The process as claimed in claim 1, characterized in that the separation apparatus is operated at a temperature of from 100° C. to 140° C.

10. The process as claimed in claim 1, characterized in that a carbon monoxide partial pressure of from 0.1 MPa to 0.3 MPa is set in the gas phase in the depressurization vessel.

11. The process as claimed in claim 6, characterized in that the filter has a pore size of from 0.5 µm to 10 µm.

12. A process for working up a liquid output from a hydroformylation reaction, which output contains aldehyde, high-boiling by-products of the hydroformylation reaction, a homogeneously dissolved rhodium complex catalyst, unreacted olefinically unsaturated compound, synthesis gas and volatile by-products, in which
    a) the liquid hydroformylation output is depressurized in a depressurization vessel, resulting in separation into a liquid phase and a gas phase; and
    b) the liquid phase obtained in the depressurization vessel is introduced into a separation apparatus in which separation into a liquid phase containing essentially high-boiling by-products of the hydroformylation reaction, the homogeneously dissolved rhodium complex catalyst and small amounts of the aldehyde and a gas phase containing the predominant amount of the aldehyde is carried out; and c) a liquid, rhodium-containing output is discharged from the separation apparatus, characterized in that the liquid, rhodium-containing output discharged from the separation apparatus is passed through a filter and solids separated off are removed from the process while the filtrate obtained is recirculated to the hydroformylation reaction;

and further characterized in that part of the liquid, rhodium-containing output discharged from the separation apparatus is removed from the process.

13. The process as claimed in claim 12, characterized in that the separation apparatus is operated at a temperature of up to 160° C.

14. The process as claimed in claim 12, characterized in that a carbon monoxide partial pressure of from 0.05 to 0.35 MPa is set in the gas phase in the depressurization vessel.

15. The process as claimed in claim 12, characterized in that a plurality of depressurization vessels having pressures which decrease from stage to stage are employed.

16. The process as claimed in claim 12, characterized in that glass fibers, metal fibers or polymer fibers are used for the filter.

17. The process as claimed in claim 16, characterized in that the filter has a pore size of from 0.1 to 20 μm.

18. The process as claimed in claim 12, characterized in that fresh rhodium and free organic phosphorus(III) compound are added to the filtrate before entry into the hydroformylation reaction.

19. The process as claimed in claim 12, characterized in that the separation apparatus is operated at a temperature of from 100° C. to 140° C.

20. The process as claimed in claim 12, characterized in that a carbon monoxide partial pressure of from 0.1 MPa to 0.3 MPa is set in the gas phase in the depressurization vessel.

* * * * *